(12) United States Patent
Sauer et al.

(10) Patent No.: US 7,079,132 B2
(45) Date of Patent: Jul. 18, 2006

(54) SYSTEM AND METHOD FOR THREE-DIMENSIONAL (3D) RECONSTRUCTION FROM ULTRASOUND IMAGES

(75) Inventors: Frank Sauer, Princeton, NJ (US); Ali Khamene, Plainsboro, NJ (US); Benedicte Bascle, Plainsboro, NJ (US)

(73) Assignee: Siemens Corporate Reseach Inc., Princeton, NJ (US)

( * ) Notice: Subject to any disclaimer, the term of this patent is extended or adjusted under 35 U.S.C. 154(b) by 522 days.

(21) Appl. No.: 10/222,182

(22) Filed: Aug. 16, 2002

(65) Prior Publication Data

US 2003/0117393 A1 Jun. 26, 2003

Related U.S. Application Data

(60) Provisional application No. 60/312,872, filed on Aug. 16, 2001, provisional application No. 60/312,876, filed on Aug. 16, 2001, provisional application No. 60/312,871, filed on Aug. 16, 2001, provisional application No. 60/312,875, filed on Aug. 16, 2001, provisional application No. 60/312,873, filed on Aug. 16, 2001.

(51) Int. Cl.
*G06T 15/00* (2006.01)

(52) U.S. Cl. ............ 345/419; 345/420; 345/424; 600/447

(58) Field of Classification Search ........... 345/419, 345/420, 424; 600/447
See application file for complete search history.

(56) References Cited

U.S. PATENT DOCUMENTS

| 5,787,889 | A | * | 8/1998 | Edwards et al. | 600/443 |
| 5,810,007 | A | * | 9/1998 | Holupka et al. | 600/439 |
| 5,928,151 | A | * | 7/1999 | Hossack et al. | 600/443 |
| 5,964,727 | A | * | 10/1999 | Edwards et al. | 604/22 |
| 6,047,080 | A | * | 4/2000 | Chen et al. | 382/128 |
| 6,288,704 | B1 | * | 9/2001 | Flack et al. | 345/158 |
| 6,755,787 | B1 | * | 6/2004 | Hossack et al. | 600/447 |

* cited by examiner

*Primary Examiner*—Kimbinh T. Nguyen
(74) *Attorney, Agent, or Firm*—Michele J. Conover

(57) ABSTRACT

A method for local 3-dimensional (3D) reconstruction from 2-dimensional (2D) ultrasound images includes deriving a 2D image of an object; defining a target region within said 2D image; defining a volume scan period; during the volume scan period, deriving further 2D images of the target region and storing respective pose information for the further 2D images; and reconstructing a 3D image representation for the target region by utilizing the 2D images and the respective pose information.

43 Claims, 1 Drawing Sheet

Figure 1:
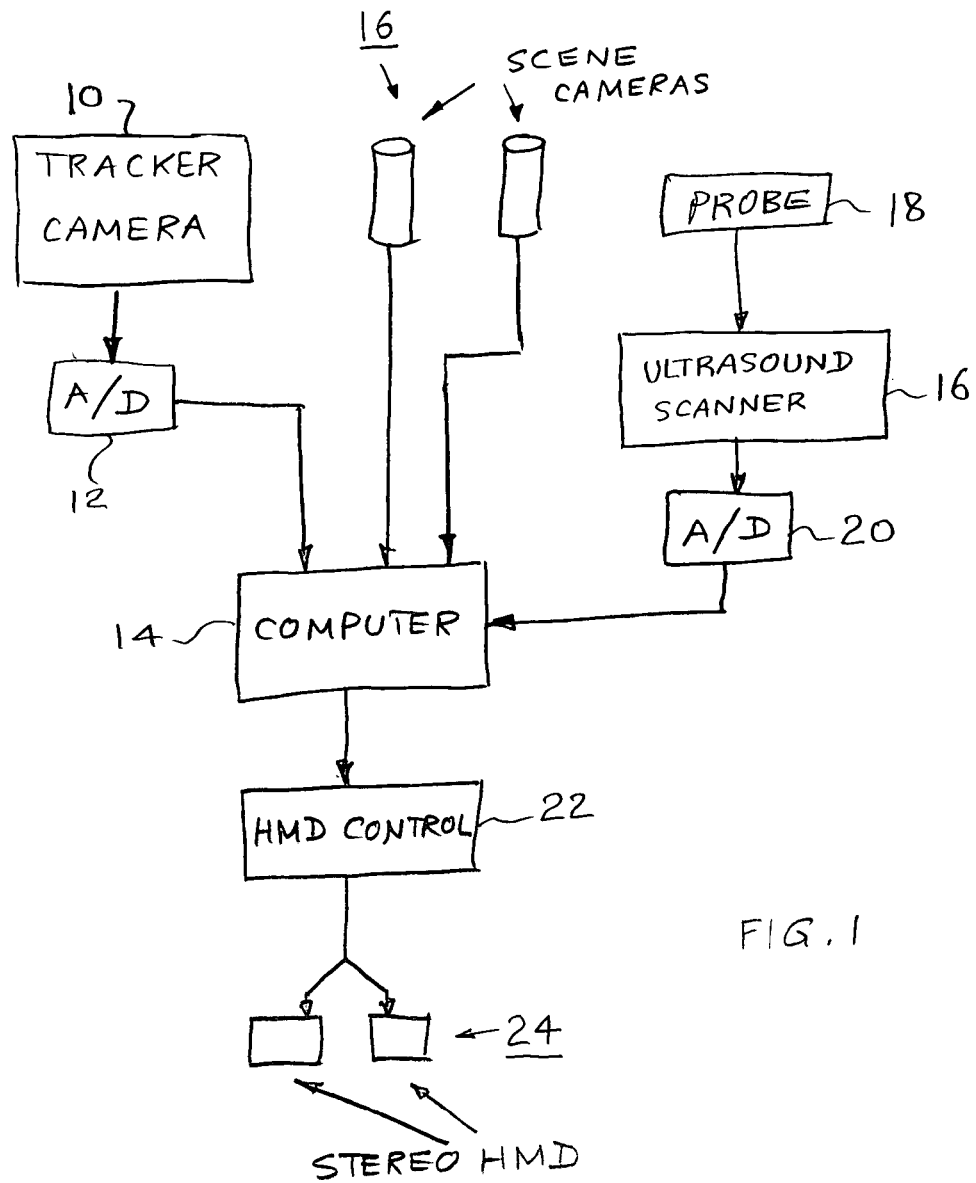

SYSTEM AND METHOD FOR THREE-DIMENSIONAL (3D) RECONSTRUCTION FROM ULTRASOUND IMAGES

Reference is hereby made to the following U.S. Provisional patent applications whereof the benefit is hereby claimed and whereof the disclosures are hereby incorporated by reference:

U.S. Provisional patent application No. 60/312,872, entitled MARKING 3D LOCATIONS FROM ULTRASOUND IMAGES and filed Aug. 16, 2001 in the names of Frank Sauer, Ali Khamene, Benedicte Bascle;

U.S. Provisional patent application No. 60/312,876, entitled LOCAL 3D RECONSTRUCTION FROM ULTRASOUND IMAGES and filed Aug. 16, 2001 in the names of Frank Sauer, Ali Khamene, Benedicte Bascle;

U.S. Provisional patent application No. 60/312,871, entitled SPATIOTEMPORAL FREEZING OF ULTRASOUND IMAGES IN AUGMENTED REALITY VISUALIZATION and filed Aug. 16, 2001 in the names of Frank Sauer, Ali Khamene, Benedicte Bascle;

U.S. Provisional patent application No. 60/312,875, entitled USER INTERFACE FOR AUGMENTED AND VIRTUAL REALITY SYSTEMS and filed Aug. 16, 2001 in the names of Frank Sauer, Lars Schimmang, Ali Khamene; and U.S. Provisional patent application No. 60/312,873, entitled VIDEO-ASSISTANCE FOR ULTRASOUND GUIDED NEEDLE BIOPSY and filed Aug. 16, 2001 in the names of Frank Sauer and Ali Khamene.

Reference is hereby made to the following copending U.S. patent applications being filed on even date herewith.

U.S. patent application, entitled MARKING 3D LOCATIONS FROM ULTRASOUND IMAGES filed in the names of Frank Sauer, Ali Khamene, Benedicte Bascle;

U.S. patent application entitled SPATIOTEMPORAL FREEZING OF ULTRASOUND IMAGES IN AUGMENTED REALITY VISUALIZATION and filed in the names of Frank Sauer, Ali Khamene, Benedicte Bascle;

U.S. patent application entitled USER INTERFACE FOR AUGMENTED AND VIRTUAL REALITY SYSTEMS and filed in the names of Frank Sauer, Lars Schimmang, Ali Khamene; and U.S. patent application entitled VIDEO-ASSISTANCE FOR ULTRASOUND GUIDED NEEDLE BIOPSY and filed in the names of Frank Sauer and Ali Khamene.

The present invention relates to ultrasound imaging, such as for medical imaging purposes and, more particularly to local three-dimensional (3D) reconstruction from two-dimensional (2D) ultrasound images.

Augmented Reality visualization of ultrasound images has been proposed in the literature; see for exampled, M. Bajura, H. Fuchs, and R. Ohbuchi. "Merging Virtual Objects with the Real World: Seeing Ultrasound Imagery within the Patient." Proceedings of SIGGRAPH '92 (Chicago, Ill., Jul. 26–31, 1992). In Computer Graphics 26, #2 (July 1992): 20

Helpful background material on augmented reality and related topics can be found in Proceedings of the IEEE and ACM International Symposium on Augmented Reality 2000, dated Oct. 5–6, 2000; Munich, Germany; IEEE Computer Society, Los Alamitos, Calif., U.S.A. In the above-cited Proceedings, an article of particular interest entitled AUGMENTED WORKSPACE: DESIGNING AN AR TESTBED is published on pages 47–53, and is authored by Frank Sauer, an inventor in the present application, et alii.

See also the review article by R. T. Azuma: "A Survey of Augmented Reality", Presence: Teleoperators and Virtual Environments, 6(4), 355–386, (1997).

FIG. 1 show a schematic block diagram of an augmented reality system as may be utilized in conjunction with features of the invention. A tracker camera 10 is coupled by way of and A/D (analog to digital) converter 12 to a programmable digital computer 14. Two scene cameras 16 are coupled to computer 14. An ultrasound scanner 16, having a transducer 18, is coupled by way of an A/D converter 20 to computer 14. A head-mounted display (HMD) control unit 22 is coupled for signal interchange with computer 14 and to an HMD display 24.

Ultrasound scanners capture live 2D images from within objects or patients (B-scans). 3D ultrasound imaging is attractive as it facilitates the diagnosis and identification of scanned structures, and provides overall a better understanding of the shape and topology of such structures. To assemble a set of 2D images into a 3D representation, one needs to track the pose of the individual 2D images, for example, using a commercial magnetic or optical tracking system.

Commercial systems are available, such as TomTec, for example, for which see website http://www.tomtec.de/). Free software to perform a 3D reconstruction from 2D ultrasound slices with known poses is available; see, for example, website http://svr-www.eng.cam.ac.uk/~rwp/stradx/. Nevertheless, it is difficult to achieve real-time performance with existing 3D ultrasound systems.

An object of the present invention is to perform local 3D reconstruction from 2D ultrasound images.

In accordance with another aspect of the invention, a method for local 3-dimensional (3D) reconstruction from 2-dimensional (2D) ultrasound images includes deriving a 2D image of an object; defining a target region within said 2D image; defining a volume scan period; during the volume scan period, deriving further 2D images of the target region and storing respective pose information for the further 2D images; and reconstructing a 3D image representation for the target region by utilizing the 2D images and the respective pose information.

The invention will be more fully understood from the following detailed description of preferred embodiments, in conjunction with the Drawing, in which FIG. 1 shows a block diagram of an augmented reality system.

In accordance with an aspect of the invention, a system for local (3D) reconstruction allows a user to identify a target in an ultrasound image, and then to scan a volume by moving the transducer. Alternatively, the system allows a user to identify a region of interest in an ultrasound image, and then to scan a volume by moving the transducer.

The system will perform a 3D reconstruction of the local volume that is centered around the target or, in the alternative, bounded by the 2-D region of interest, and the scan motion. The local volume is smaller than the whole volume scanned by the ultrasound slice, and the 3D reconstruction can accordingly be performed in real time.

Preferably, the 3D information is visualized in an augmented reality fashion. The ultrasound images are overlaid onto a view of the patient or the object in a registered way. Structures visible in the ultrasound images appear in the location of the corresponding physical structures. Preferably, the augmented view is stereoscopic to provide the user with depth perception. For the augmented reality visualization, the system includes means to track the ultrasound transducer's pose from the user's viewpoint.

A preferred embodiment in accordance with the principles of the present invention comprises and ultrasound scanner, including a transducer and tracking apparatus to track the transducer. For the option with augmented reality (AR) applications, tracking apparatus is utilized to track user's viewpoint. A calibration procedure is established, and a computer is utilized for generating graphics.

As concerns visualization, the volume can be shown as a 3D texture map. Alternately, the system can process the volume information and segment out a target structure. A segmented structure is then displayed in a 3D surface representation.

With regard to the user interface, there are various ways for the user to input the location of the target structure of interest, including such as are described in the afore-mentioned patent application entitled "MARKING 3D LOCATIONS FROM ULTRASOUND IMAGES".

Target localization and marking can be done by using a pointing device, such as a computer-type mouse to mark a 2D location in the image. With the knowledge of the 3D pose of that image, the system can calculate the 3D position of the marker. The user's input may be in an "on-line" mode, where he holds the transducer still in the desired pose, or in an "off-line" mode, where he first freezes (that is, records) the image together with its pose information, and then places the marker in the recorded still image at his leisure. For the on-line mode, the pointing device is preferably attached to the transducer and can be operated with the same hand that is holding the transducer, or alternatively, is placed on the floor and is foot-actuated by the user.

Preferably, the system performs image processing on an ultrasound image and automatically or semiautomatically locates a target. The type of target may have optionally been predetermined by the user. Hence, the input of the user is simplified. For example, without an extra pointing device, the user may place the transducer in a pose where the target structure appears on the vertical center-line of the ultrasound image. The user then simply triggers the system to locate the target along the image's center-line—with a button on the transducer, with a foot switch, or by voice control, and so forth.

The system includes a processor that searches the image along its centerline, which makes locating the target easier than if the search would have had to be conducted over the whole image. A preferred search algorithm would be to de-noise the image around the centerline, e.g. with a median filter, identify potential target locations in a line scan along the centerline, and verify the existence of a target with a Hough transform. The Hough transform is known and may be found in various textbooks, such as, for example, "Fundamentals of Electronic Image Processing" by Arthur R. Weeks, Jr., IEEE Press, New York, N.Y.; 1996. When the system proposes a target location, the user then accepts or rejects it with another simple trigger input (such as button on transducer, footswitch, voice, and so forth).

Alternatively, a line on the ultrasound image may be utilized as pointer. A line other than a vertical centerline can be used, such as a vertical off-center line, or a line that is tilted at an angle with respect to vertical direction. Also, target position along line can be input by user via thumbwheel at the transducer or by using a similar 1-D pointing device, (no image processing being necessary.

Alternatively the user can use a line on the ultrasound image to point to a target from two different transducer poses, so that the system can calculate the target location as the intersection of the two lines in 3D space; two different lines can be used to require less movement between the two pointing transducer poses, e.g. two lines that intersect in the image.

The image processing is powerful enough to find a target in the 2D image. Then the user need only position the transducer so that the target is visible in the image, initiate the automatic target search, and then confirm or dismiss a target proposed by the system.

Several targets can be found in the same image. This embodiment is attractive from a user point of view as it requires the least input, but robust target detection in ultrasound images is generally very difficult. Therefore, it is preferable to provide the user with a 1D or 2D pointing interface as described in the above.

The size of a region of interest centered at the target can be fixed, but is preferably user-adjustable. Once size and location of a region of interest is determined in a 2D ultrasound slice, the user triggers the start and the end of the volume scan, e.g. by using a pushbutton at the transducer, or with a foot switch, or via voice command, etc. The system records 2D images together with the pose information from the tracking system and builds the volume according to prior art.

In an alternate embodiment, the system automatically selects target structures for local reconstruction. An important example is local 3D reconstruction from ultrasound Doppler images. The system automatically detects the regions with flow and performs local volume reconstruction or segmentation for these regions.

While the invention has been explained by way of exemplary embodiments, it will be understood by one of skill in the art to which it pertains that various modifications and changes may be readily made without (departing from the spirit of the invention which is defined by the claims following.

What is claimed is:

1. A method for local 3-dimensional (3D) reconstruction from 2-dimensional (2D) ultrasound images, comprising:
   deriving a 2D image of an object, together with corresponding pose information;
   defining a 2D target region within said 2D image, the 2D target region having a user-defined size and location;
   defining further a local target volume within the object, the target volume having a user-defined size and location;
   deriving a set of further 2D images having respective poses and intersecting said local target volume, said set of further 2D images scanning through the local target volume; and
   reconstructing a 3D image representation of said local target volume from said set of 2D images and said respective poses.

2. A method for local 3D reconstruction as recited in claim 1, wherein said step of defining a target region comprises a step of searching said image along its centerline for identifying a potential target region.

3. A method for local 3D reconstruction as recited in claim 2, wherein said step of searching said image comprises a step of utilizing a search algorithm for searching said image along its centerline for identifying a potential target region.

4. A method for local 3D reconstruction as recited in claim 3, wherein said step of utilizing a search algorithm comprises a step of do-noising said image around its centerline for identifying a potential target region.

5. A method for local 3D reconstruction as recited in claim 4, wherein said step of de-noising comprises a step of median filtering for identifying a potential target region.

6. A method for local 3D reconstruction as recited in claim 3, wherein said step of searching said image comprises a step of utilizing a Hough transform for verifying a potential target region.

7. The method of claim 1 wherein the step of defining a 2D target region further comprises the step of:
   marking a 2D location in the image.

8. The method of claim 1 wherein the 2D target region is rectangular.

9. The method of claim 1 wherein the lateral extent of said 3D target volume is determined by the 2D target region, and the depth of said 3D target volume is determined involving the steps of
   moving the ultrasound transducer used for said deriving of said 2D images into a start position,
   moving said ultrasound transducer into an end position, wherein the movement is essentially perpendicular to the 2D image planes.

10. The method of claim 1 wherein the step of defining a 2D target region further comprises the steps of:
    predefining a target to be found in the image;
    automatically searching for targets in the image; and
    if a target is found, marking the target.

11. A method for local 3D reconstruction as recited in claim 1, wherein said step of defining a 2D target region includes identifying a target in said 2D image.

12. A method for local 3-dimensional (3D) reconstruction from 2-dimensional (2D) ultrasound images, comprising:
    deriving a 2D image of an object;
    defining a 2D target region within said 2D image, the 2D target region having a user-defined size and location;
    defining further a local target volume within the object, the target volume having a user-defined size and location;
    defining a volume scan period;
    during said volume scan period, deriving a set of further 2D images of said target region that intersect said local target volume, said set of further 2D images scanning through the local target volume, and storing respective pose information for said set of further 2D images; and
    reconstructing a 3D image representation of said local target volume by utilizing said set of 2D images and said respective pose information.

13. A method for local 3D reconstruction as recited in claim 12, wherein said steps of defining a target region comprises semi-automatic steps.

14. A method for local 3-dimensional (3D) reconstruction from 2-dimensional (2D) ultrasound images, comprising:
    deriving a 2D image of an object;
    defining a 2D target region within said 2D image, said 2D target region being significantly smaller than the 2D image and having a user-defined size and location;
    defining further a local target volume within the object, the target volume having a user-defined size and location;
    defining the start and end of a volume scan;
    deriving a set of further 2D images of said target region during a period between said start and end of said volume scan, said set of further 2D images intersecting said local target volume and scanning through the local target volume, said set of further 2D images having respective poses; and
    reconstructing a 3D image representation fey of said local target volume by utilizing said set of 2D images and said respective pose information.

15. A method for local 3-dimensional (3D) reconstruction from 2-dimensional (2D ) ultrasound Doppler images, comprising:
    deriving a 2D Doppler image of an object;
    detecting flow regions exhibiting predetermined flow characteristics;
    defining a 2D target region within said 2D image in correspondence with said flow regions, the 2D target region having a user-defined size and location;
    defining further a local target volume within the object, the target volume having a user-defined size and location;
    defining a volume scan period;
    during said volume scan period, deriving a set of further 2D images of said 2D target region and storing respective pose information for said set of further 2D images, said set of further 2D images intersecting said local target volume and scanning through said local target volume; and
    reconstructing a 3D image representation of said local target volume by utilizing said set of 2D images and said respective pose information.

16. Apparatus for local 3-dimensional (3D) reconstruction from 2-dimensional (2D) ultrasound images, comprising:
    means for deriving a 2D image of an object;
    means for defining a 2D target region within said 2D image, the 2D target region having a user-defined size and location;
    means for defining further a local target volume within said object, the target volume having a user-defined size and location;
    means for defining a volume scan period;
    means for defining size and location of 2D target region;
    means for defining size and location of 3D target volume;
    means for storing respective pose information for a set of further 2D images of said target region derived during said volume scan period by said means for deriving a 2D image said set of further 2D images intersecting said local target volume and scanning through the local target volume; and
    means for reconstructing a 3D image representation of said local target volume by utilizing said set of 2D images and said respective pose information.

17. Apparatus for local 3-dimensional reconstruction as recited in claim 16, wherein said means for defining a target region comprises processor means for searching said image along its centerline for identifying a potential target region.

18. Apparatus for local 3-dimensional (3D) reconstruction as recited in claim 17, wherein processor means for searching utilizes a search algorithm for searching said image along its centerline for identifying a potential target region.

19. Apparatus for local 3-dimensional (3D) reconstruction as recited in claim 17, wherein processor means for searching utilizes a search algorithm for de-noising said image around its centerline for identifying a potential target region.

20. Apparatus for local 3-dimensional (3D) reconstruction as recited in claim 17, wherein processor means for searching utilizes a search algorithm for de-noising said image around its centerline, by using a median filter, for identifying a potential target region.

21. Apparatus for local 3-dimensional (3D) reconstruction as recited in claim 17, wherein processor means for searching utilizes a Hough transform for verifying a potential target region.

22. The method of claim 7 wherein a pointing device is used to mark the location in the image.

23. The method of claim 7 wherein said marked 2D location is used in conjunction with said corresponding pose information to mark a corresponding 3D location.

24. The method of claim 7 wherein a user can adjust the size of the 2D target region.

25. The method of claim 7 wherein the 2D target region is centered at said marked 2D location.

26. The method of claim 22 wherein the pointing device is a computer mouse.

27. The method of claim 22 where the pointing device is the tracked head movement of the user.

28. The method of claim 8 wherein the step of defining a 2D target region further comprises the step of:

determining width and height of said 2D target region.

29. The method of claim 8 wherein said 3D target volume has a rectangular cross-section, and height and width of said 3D target volume are identical to the height and width of said 2D target region.

30. The method of claim 28 wherein width and/or height are predefined.

31. The method of claim 28 wherein the user sets width and/or height according to the size of the target.

32. The method of claim 28 wherein an automatic algorithm sets width and/or height according to the size of the target.

33. The method of claim 29 wherein the depth of said 3D target volume is pro-set or pro-selected.

34. The method of claim 29 wherein the depth of said 3D target volume is set proportional to its height or width.

35. The method of claim 29 wherein the user sets the depth of said 3D target volume according to the size of the target.

36. The method of claim 29 wherein an algorithm sets the depth of said 3D target volume according to the size of the target.

37. The method of claim 23 wherein said 3D target volume is centered at said marked 3D location.

38. The method of claim 9 wherein a trigger device is used to identify said start and end positions.

39. The method of claim 38 wherein said trigger device is a computer mouse.

40. The method of claim 38 wherein said trigger device is a foot switch.

41. The method of claim 38 wherein said trigger device is located at the transducer.

42. The method of claim 10 wherein a user can adjust the size of the 2D target region.

43. The method of claim 42 further comprising the steps of:

triggering a start and end for a volume scan of the target;

building a 3D target volume from the volume scan.

* * * * *